United States Patent
Watson

[11] Patent Number: 5,914,095
[45] Date of Patent: Jun. 22, 1999

[54] POLYCHELANTS CONTAING AMIDE BONDS

[75] Inventor: Alan D Watson, Campbell, Calif.

[73] Assignee: Salutar, Inc., Sunnyvale, Calif.

[21] Appl. No.: 07/772,349

[22] Filed: Oct. 7, 1991

Related U.S. Application Data

[63] Continuation-in-part of application No. PCT/EP91/00565, Apr. 5, 1990, and application No. 07/464,865, Jan. 16, 1990, Pat. No. 5,364,613, which is a continuation-in-part of application No. 07/335,162, Apr. 7, 1989, abandoned.

[51] Int. Cl.$^6$ ..................................................... A61B 5/055
[52] U.S. Cl. .................. 424/1.65; 424/9.365; 424/9.363; 534/15; 534/16; 556/50; 556/55; 556/63; 556/77; 556/105; 556/116; 556/134; 556/148; 514/492; 514/502; 514/836
[58] Field of Search ............................... 424/9.365, 1.65, 424/9.363; 436/173; 556/50, 55, 63, 77, 105, 116, 134, 148; 514/492, 502, 936; 600/458; 534/15, 16

[56] References Cited

U.S. PATENT DOCUMENTS

| | | | |
|---|---|---|---|
| 4,587,329 | 5/1986 | Tomalia et al. | 528/363 |
| 4,639,365 | 1/1987 | Sherry | 424/9 |
| 4,647,447 | 3/1987 | Gries et al. | 424/9 |
| 4,678,667 | 7/1987 | Meares et al. | 424/85 |
| 4,855,353 | 8/1989 | Kurami et al. | 525/54.1 |
| 4,857,599 | 8/1989 | Tomalia et al. | 525/259 X |
| 4,871,779 | 10/1989 | Killat et al. | 521/28 |
| 4,923,985 | 5/1990 | Ganson et al. | 540/474 |
| 4,986,980 | 1/1991 | Jacobsen | 424/9 |
| 5,155,215 | 10/1992 | Ranney | 534/16 |
| 5,204,448 | 4/1993 | Subramanian | 530/391.5 X |
| 5,338,532 | 8/1994 | Tomalia et al. | 424/1.49 |
| 5,364,613 | 11/1994 | Sieving et al. | 424/9 |

FOREIGN PATENT DOCUMENTS

| | | |
|---|---|---|
| B-77159-87 | 3/1988 | Australia . |
| B-11685-88 | 8/1988 | Australia . |
| 0 292 689 | 11/1988 | European Pat. Off. . |
| 0 305 320 | 3/1989 | European Pat. Off. . |
| 8801178 | 2/1988 | U.S.S.R. ........................ A61K 49/02 |
| WO 89/12631 | 12/1989 | WIPO . |
| WO 90/12050 | 10/1990 | WIPO . |

OTHER PUBLICATIONS

Alberts et al. *Molecular Biology of the Cell*, Garland Publishing, Inc., Nerw York, 1983.
Bryden and Rielley, *Anal. Chem.*, 63:1418–1425, 1981.
Cacheria et al., *Inorg. Chem.*, 26:958–960, 1987.
Campbell et al., *Basic Biochemistry for Medical Students*, Academic Press, Inc., London, 1975.
Conn and Stumpf, *Outlines of Biochemistry*, John Wiley & Cons, Inc., New York, 1976.
Cunningham, *Understanding Immunology*, Academic Press, New York, 1978.
Delgado and Da Silva, *Talanto*, 29:815–822, 1982.
Desreux, *Inorg. Chem.*, 19:1319–1324, 1980.
Kowalsky and Perry, *Radiopharmaceuticals in Nuclear Medicine Practice*, Appleton & Lange, Norwalk, CT, 1987.
Lehninger, *Biochemistry*, Worth Publishers, Inc. New York, 1970.
Meares and Wensel, *Acc. Chem Res.*, 17:202–209, 1984.
Mettler Jr. and Guiberteau, *Essentials of Nuclear Medicine Imaging*, Harcourt Brace Jovanovich, Publishers, New York, 1985.
Moi et al., *Inorg. Chem.*, 26:3458–3463, 1987.
Stryer, *Biochemistry*, W.H. Freeman and Company, San Francisco, 1975.
Tomalia et al., *Polymer Journal*, 17:117–132, 1985.
White et al., *Principles of Biochemistry*, McGraw–Hill Kogakusha, Ltd., London, 1973.
*Encyclopedia of Polymer Science and Engineering*, John Wiley & Sons, New York, 1982.

Primary Examiner—Gary E. Hollinden
Attorney, Agent, or Firm—Fish & Richardson P.C.

[57] ABSTRACT

There are provided polychelants and their metal chelates which are useful in diagnostic imaging and in radiotherapy and which comprise a plurality of macrocyclic chelant moieties, e.g. DOTA residues, conjugated to a dendritic polyamine backbone molecule, e.g. a starburst dendrimer. To produce a site-specific polychelate, one or more of the macrocyclic chelant carrying backbone molecules may be conjugated to a site-directed macromolecule, e.g. a protein.

23 Claims, No Drawings

POLYCHELANTS CONTAING AMIDE BONDS

This application is a continuation-in-part of application Ser. No. 07/464,865 filed Jan. 16, 1990, now U.S. Pat. No. 5,364,683 itself a continuation-in-part of application Ser. No. 07/335,162, filed Apr. 7, 1989, now abandoned. This application is also a continuation-in-part of the U.S. National Phase of PCT/EP91/00565 (International Filing Date Apr. 5, 1990) which is also a continuation-in-part of application Ser. No. 07/464,865.

FIELD OF THE INVENTION

This invention relates to chelants, especially polychelants, in particular bifunctional polychelants, and more particularly site-directed macromolecular conjugates of macrocyclic chelants, and the chelates and salts thereof and macrocyclic intermediates therefor, and their applications in medicine, including the field of diagnostic imaging. The polychelates are especially suited to enhance images of selected mammalian organs, tissues, cells, and the like, in vivo, using Magnetic Resonance Imaging, X-ray, gamma scintigraphy, and CT scanning, by virtue of their enhanced imaging properties and site specificity. The polychelants are also well suited for metal detoxification, therapeutic delivery of radioisotopes and diagnostic nuclear medicine applications.

BACKGROUND OF THE INVENTION

Medical imaging modalities, such as MRI, X-ray, gamma scintigraphy, and CT scanning, have become extremely important tools in the diagnosis and treatment of illnesses. Some imaging of internal parts relies on inherent attributes of those parts, such as bones, to be differentiated from surrounding tissue in a particular type of imaging, such as X-ray. Other organs and anatomical components are only visible when they are specifically highlighted by particular imaging techniques.

One such technique with potential to provide images of a wide variety of anatomical components involves biotargeting image-enhancing metals. Such a procedure has the possibility of creating or enhancing images of specific organs and/or tumors or other such localized sites within the body, while reducing the background and potential interference created by simultaneous highlighting of non-desired sites.

Researchers have recognized for many years that chelating various metals increases the physiologically tolerable dosage of such metals and so permits their use in vivo to enhance images of body parts (see for example C. D. Russell and A. C. Speiser, J. Nucl. Med., 21, 1086 (1988) and U.S. Pat. No. 4,647,447 (Gries et al.)). However, such simple metal chelate image enhancers, without further modification, do not generally provide any particularly significant site specificity.

The attachment of metal chelates to tissue or organ targeting macromolecules, e.g. biomolecules such as proteins, in order to produce site specific therapeutic or diagnostic agents has been widely suggested.

Many such bifunctional chelating agents, i.e. agents which by virtue of the chelant moiety and capable of strongly binding a therapeutically or diagnostically useful metal ion and by virtue of the site-specific macromolecular component are capable of selective delivery of the chelated metal ion to the body site of interest, are known or have been proposed in the literature. Thus for example even relatively early publications in the field of MRI contrast agents, such as CB-A-2169598 (Schering) and EP-A-136812 (Technicare) suggested the use as contrast agents of paramagnetic metal ion chelates of bifunctional chelants.

The attachment or chelant moieties to site-specific macromolecules has been achieved in a number of ways, for example the mixed anhydride procedure of Krejcarek et al. (Biochemical and Biophysical Research Communications 77: 581 (1977)), the cyclic anhydride procedure of Hnatowich et al. (see Science 220: 613 (1983) and elsewhere), the backbone derivatisation procedure of Meares et al. (see Anal. Biochem. 142: 68 (1984) and elsewhere—this is a technique used by Schering in EP-A-331616 to produce site specific polychelates for use as MRI or X-ray contrast agents), and the linker molecule procedure used for example by Amersham (see WO-A-85/05554) and Nycomed (see EP-A-186947 and elsewhere) to produce paramagnetic metal ion chelates of bifunctional chelants for use as MRI contrast agents.

Thus, Krejcarek et al. (supra) disclosed how polyaminopolycarboxylic acid (PAPCA) chelants, specifically DTPA (diethylenetriaminepentaacetic acid) could be conjugated to a protein, such as human serum albumin (HSA), by reaction of the triethylamine salt of the PAPCA with isobutylchloroformate (IBCF) and by reacting the IBCF-PAPCA adduct with the protein. Their aim was to attach one radioactive metal per human serum albumin molecule for the purpose of measuring biological function.

Site specific uses of various imaging techniques all require or would be enhanced by use of a multiplicity of the appropriate metal ion conjugated to a site directed macromolecule. For example, it is believed that a 50% reduction in $T_1$ relaxation time of water protons in a target tissue is a requirement for an effective MRI contrast agent. Considering the affinity of antibodies for their antigens and the concentration of these antigens in the target tissues, it has been calculated that each antibody molecule must carry a number of paramagnetic centers to bring about these levels of $T_1$ reduction. (See Eckelman, et al., NATO ASI Series, Series A, 152:571 (1988)).

Unger et al. in Investigative Radiology 20:693 (1985) analyzed tumor enhancement for magnetic resonance imaging using an anti-CEA monoclonal antibody conjugated with Gd-DTPA. They found no tumor enhancement when 4 Gd atoms were bound per antibody molecule, and predicted that a far greater ratio of imaging metal atoms per macromolecule would be required to be effective.

Likewise, Schreve and Aisen in Mag. Res. in Medicine 3, 336 (1986), concluded that the concentrations of paramagnetic ion which could be delivered to a tumor using the described technology would result in large doses for humans, making this approach to imaging highly limited in its use.

For site specific image enhancement however it is important that the site specificity of the tissue or organ targeting moiety of such chelates of bifunctional chelants should not be destroyed by conjugation of the chelant moiety. Where the bifunctional chelant contains only one chelant moiety this is not generally a severe problem; however when attempts have been made to produce bifunctional polychelants by conjugating several chelant moieties onto a single site-specific macromolecule, it has been found not only may the maximum achievable chelant: site-specific macromolecule ratio be relatively limited but as the ratio achieved increases the site-specificity of the resulting bifunctional polychelant decreases.

Numerous attempts have nonetheless been made to produce bifunctional polychelants with increased numbers of chelant moieties per site-specific macromolecule.

Thus Hnatowich et al. (supra) used the cyclic anhydride of the chelant DTPA to attach it to a protein.

This is a relatively simple one-step synthesis procedure which as a result has been used by many other researchers. However, due to the presence of two cyclic anhydride groups in the starting material, widespread cross-linking of the macromolecules can lead to the production of conjugates that cannot readily be characterized (see Hnatowich et al., J. Immul. Methods 65:147 (1983)). In addition, this procedure suffers from the same drawback as that for Krejcarek's mixed anhydride method in that the uncontrolled addition of more than a few chelant moieties destroys the site-specificity of the macromolecule to which they are linked. (See also Paik et al. J. Nucl. Med. 25:1158 (1983)).

In order to overcome the problems of attaching larger numbers of chelant moieties to a site specific macromolecule without destroying its site-specificity, i.e. without disturbing its binding site(s), there have been many proposals for the use of a backbone molecule to which large numbers of chelant moieties can be attached to produce a polychelant one or more of which can then be conjugated to the site-specific macromolecule to produce the bifunctional polychelant.

The by now conventional cyclic anhydride conjugation technique of Hnatowich et al. (supra) has thus been used to produce bifunctional polychelants in which the chelant moieties are residues of open chain PAPCAs, such as EDTA and DTPA, and in which the backbone molecule is a polyamine such as polylysine or polyethyleneimine. Thus for example Manabe et al. in Biochemica et Biophysica Acta 883: 460–467 (1986) reported attaching up to 105 DTPA residues onto a poly-L-lysine backbone using the cyclic anhydride method and also attaching polylysine polyDTPA polychelants onto monoclonal antibody (anti-HLA $IgG_1$) using a 2-pyridyl disulphide linker achieving a substitution of up to about 42.5 chelants (DTPA residues) per site-specific macromolecule. Torchlin et al. in Hybridoma 6:229–240 (1987) also reported attaching DTPA and EDTA to polyethyleneimine and polylysine backbones which were then attached to a myosin-specific monoclonal antibody, or its Fab fragment, to produce bifunctional polychelants for use in MRI or scintigraphy.

While Manabe and Torchlin have reported the production of bifunctional polychelants, the cyclic anhydride route adopted by Manabe poses cross-linking and hence characterization problems and Torchlin et al in their conclusion doubted that their technique would enable the paramagnetic metal concentration to be increased sufficiently to permit MRI of tumours.

There is thus a continuing need for improved bifunctional polychelants and the present invention resides in the provision of novel and improved bifunctional polychelants, particularly such polychelants that can be produced from relatively non-complex chelant starting materials. More particularly, the present invention resides in the provision of bifunctional polychelants, and their chelates, containing macrocyclic chelant moieties, that is to say chelants which contain at least one macrocyclic structural element which serves at least in part to define the seat for the chelated ion. Macrocyclic chelants, (for example 1,4,7,10-tetraazacyclododecane tetraacetic acid) are themselves well known as chelants capable of forming very stable chelate complexes, and in particular complexes which unlike those of non-macrocyclic chelants are particularly stable kinetically as well as themodynamically, but they cannot be effectively linked to backbone molecules such as polylysine by the prior art cyclic anhydride (Hnatowich) or mixed anhydride (Krejcarek) procedures, as the procedures are presently applied.

This invention provides an efficient and successful means for creating bifunctional poly(macrocyclic chelants) (BPMCs) as well as the BPMCs and their chelates themselves. Numerous obstacles previously present in creating a biologically functional imaging molecule with a multiplicity of chelating sites have been overcome, and in particular cross linking of the polychelants has been avoided, allowing for better solubility and better site-specificity, due to the workable size of the bifunctional polychelant.

SUMMARY OF THE INVENTION

The present invention relates to novel compounds useful in X-ray and MRI image enhancement, as well as therapeutic and diagnostic nuclear medicine. One class of these novel compounds is composed of a dendrimer, preferably a starburst dendrimer, backbone molecule to which a multiplicity of macrocyclic chelant moieties are attached. (The term "starburst dendrimer" is explained hereafter and also by Tomalia in U.S. Pat. No. 4,587,329.) These polychelant compounds and the chelates and salts thereof are here termed magnifiers. The chelant moieties in the magnifiers are capable of chelating metal ions with a high level of stability, and are metallated with the appropriate metal ion(s) to enhance images and/or to deliver cytotoxic doses of radioactivity.

These magnifiers can be attached by well-known methods to a site-directed macromolecule, e.g. a protein, to form BPMCs which can enhance images and/or deliver cytotoxic doses of radioactivity to the targeted cells, tissues, organs, and/or body ducts.

As an intermediate in the process of making the magnifiers, alkylhaloformate adducts of macrocyclic chelants are formed and these represent a further aspect of the invention.

The magnifiers are in and of themselves useful entities in medical diagnosis and therapy, due in part to their unique localization in the body. The monomeric chelates presently used for MRI contrast enhancement (e.g., $Gd(DTPA)^{2-}$, $Gd(DOTA)^{1-}$) have in vivo applications related to their specific, rapid biodistribution, localizing these chelates in the extravascular/extracellular spaces of the body. The size of the magnifier, typically 1–6 kD, especially 2–4 kD, radically alters the biodistribution of the chelates. The magnifiers generally have extended intravascular residence times, generally of the order of hours, and usually will eventually clear into the extracellular fluid (ECF) space and undergo renal excretion. Thus as these magnifiers remain primarily in the intravascular system for a diagnostically useful residence time, they are suitable for a range of uses from blood pool and cardiac perfusion imaging, CNS tumour detection and volume determination to thrombus detection and angiography. These diagnoses are not readily accessible with an agent which rapidly disperses into the extracellular/extravascular space and moreover in view of their enhanced relaxivity the MRI contrast agents according to the invention can be administered at significantly reduced dosages relative to correct monomeric MRI contrast agents such as GdDTPA and GdDOTA, providing a significantly improved safety margin in their use.

The invention also enables water-soluble MRI contrast agents to be produced which can safely be administered orally for efficient liver imaging. For such agents the dendrimeric chelant would preferably be used as the vehicle for Mn(II) or Gd(III) paramagnetic ions for optimum MR efficiency.

Furthermore, by suitable selection of chelated specifies, chelates according to the invention may be produced which are capable of functioning as X-ray agents (for example by choosing tungsten) and also as both MR and X-ray contrast agents by choosing an appropriate lanthanide metal ion.

Attachment of the magnifier to a site-directed macromolecule results in even greater in vivo target specificity. The macromolecule is preferably an antibody, other protein or other molecule which will travel in vivo to that site to deliver the chelated metals. In the present invention the capacity of this site-directed macromolecule to travel and/or bind to its target is not comprised by the addition of the chelated metals. The number of chelates per molecule is sufficient to enhance the image of that particular target. The BPMCs are distinct entities, and desirably are substantially non-crosslinked.

In one embodiment the magnifiers of the invention can be represented by the formula I $$B(L)_n \qquad (I)$$

where
B is the residue of a dendrimeric polyamine backbone molecule, typically a molecule containing terminal amine groups extending radially outwards from a central core moiety,
each L is independently the residue of a macrocyclic chelant of 3 to 200, preferably up to 100, particularly up to 50.

Using this formula for the magnifiers, the corresponding BPMCs of the invention can be represented by the formula II $$T(B'(L)_n)_m \qquad (II)$$

where T is the residue of a dendrimers site-directed macromolecule, each $B'(L)_n$ is independently the residue of a magnifier of formula I, optionally incorporating a residue X' of a linker molecule which serves to link the magnifier to the macromolecule, and m is a positive integer, e.g. 1 to 10, preferably 1,2,3 or 4.

The dendrimeric backbone molecule to which the macrocyclic chelants are bound preferably has a multiplicity of amines arranged to extend radially outwards form a central core moiety i.e. a starburst dendrimer-type backbone molecule. Such starburst dendrimer-type backbone molecules comprise a central core moiety to which a plurality of linker groups are attached. The linker groups may either be bonded directly to the macrocyclic chelates or may, optionally preferably be terminally branched by the addition of further linking moieties which may each be the same or different to the main branch linker group. A backbone molecule wherein all the linker groups have been terminally branched once is termed a first-generation ($C_{1.0}$) backbone molecule. Further terminal branching of the linker groups is first-generation backbone molecules will provide second, third, fourth etc. generation backbones. With each successive round of branching, the number and attachment points available for bonding the macrocyclic chelant groups increases.

The linkage between the backbone B and the macrocyclic chelant moiety is preferably via an amide bond, the amide nitrogen deriving from the backbone molecule and the amide carbonyl group deriving from a carboxyl or carboxyl derivative functionality on the macrocyclic chelant. Particularly preferably the macrocyclic chelant is a PAPCA and especially preferably the carboxyl or carboxyl derivative functionality is attached to the or a ring structure of the macrocyclic chelant at a donor ring heteroatom, especially a nitrogen.

Magnifiers and BPMCs can be used in their unmetallated or undermetallated state for absorption or available metal ions in vivo, such as in metal detoxification. Alternatively, magnifiers and BPMCs can be used in their metallated form to deliver chelated metal ions for diagnostic or therapeutic applications.

Metal ions are chosen for chelation by the magnifiers for their ability to perform their diagnostic or therapeutic role. These roles include but are not limited to enhancing images in MRI, gamma scintigraphic or CT scanning, or X-rays, or delivering cytotoxic agents to kill undesirable cells such as in tumors.

For use with radionuclides, such as in nuclear medicine, this invention provides the advantage of tight binding of the radionuclides by the macrocyclic chelants. This allows a more specific image due to lower background levels of the metals.

Preferably, metal incorporation is accomplished prior to attachment of the magnifier(s) to a site-directed macromolecule. The metal is titrated from sub-stoichiometric levels up to full incorporation, thus eliminating the need for dialysis and extensive chromatographic purification. In this manner significant losses as well as dilution are avoided. Non-specific binding of the metal ions to the macromolecules is also prevented. However, application of the invention to radionuclides with short half-lives may require metallation of the BPMC as a final step, followed by simple rapid purification (e.g. gel filtration) to remove excess unbound radionuclide.

In the BPMC, preferably one or two backbone molecules are linked to the site-directed macromolecule. By limiting the number of magnifiers linked to the macromolecule the pharmacological behavior of the BPMC would be expected to show high target specificity and low-non-specific binding.

The BPMCs are capable of containing a large number of macrocyclic chelant moieties. This allows site-specific imaging to be enhanced beyond the levels previously available.

These magnifiers and BPMCs are not only extremely useful for magnetic resonance imaging, they are also useful in other forms of imaging, as well as in nuclear medicine. Osmolality of currently available image enhancing agents contributes to some of the undesirable side effects of these agents, including pain to the patient. By allowing a marked increase in the number of image enhancing chelated metal centres per molecule in solution, this invention allows for a significant decrease in osmolality, while retaining the same level or increasing the level of image enhancement.

DETAILED DESCRIPTION

Backbone Molecule

The magnifiers of the invention are produced by conjugating a plurality of macrocyclic chelants onto a dendrimeric backbone molecule, generally a water-soluble polymer having reactive groups. The backbone polymer will conveniently have a least 3 and preferably up to 96, especially up to 48, e.g. 3, 6, or 12 reactive groups. The backbone molecule conveniently is a branched-chained polymer, such as a starburst dendrimer. The reactive groups can be amines, preferably primary amines, carboxylates, alcohols or thiolates etc.

The starburst dendrimers include polyaminoamido dendrimers (PAMAM) and related starburst dendrimers. Whilst sixth generation dendrimers (192 primary amines) and higher have been prepared, lower generation dendrimers are preferred, especially $G_0$, $G_1$, $G_2$ and $G_3$ dendrimers (which have respectively 3, 6, 12 and 24 free amines). Preparation of PAMAM and related dendrimers is described by Tomalia et al. in Polymer Journal 17:117 (1985) and in U.S. Pat. No. 4,587,329.

Preferably the starburst dendrimer-type backbone molecules are radially symmetrical with each optionally branched linker group being identical.

A branched linker group may be formed by the successive addition of linking moieties which may each be the same or different. A branched linker group wherein the linking moieties are all identical is preferred. Alternatively, the branched linker group may be pre-formed and subsequently conjugated to the core moiety.

The core moiety may be any molecule to which a multiplicity of linker groups can be attached.

$B^0$ $(L^0R^0)_n{}^0$ where $B^0$ is a branching site, e.g. an optionally substituted nitrogen, phosphorus, silicon or carbon atom or a homo- or heterocyclic ring, preferably having 5–8 ring members; $L^0$ is a bond or a zero generation linking group, e.g. a $C_{1-4}$ alkylene chain;

$R^0$ is a functional group capable of undergoing an addition, replacement or more preferably a condensation reaction whereby to conjugate at least one first-generation linker group L' to $B^0$ $L^0$, e.g. an amine, hydroxyl or carboxyl group or a derivations thereof, e.g. an ester or amide, and $n^0$ is an integer having a value of at least 2, preferably 3 or 4. Using analogous terminology, an Xth generation, $G_{x'}$, starburst dendrimer backbone molecule would have the general formula.

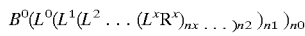

where $R^x$ is a functional group capable of being conjugated to a chelant moiety, e.g. an amine group. For the PAMAM starburst dendrimers $N^0$ is 3, each of $n^1$, $n^2$, $n^3$ etc are 2, and $R^x$ is an amine group.

Suitable core $G_o$ moieties thus include $N(CH_2CH_3COOCH_3)_3$, $(CH_3OOCCH_2CH_2)_2$ $NCH_2CH_2N$ $(CH_2CH_2COOCH_{N3})_2$, $(CH_3OOCCH_2CH_2)_2CHCH$ $(CH_2CH_2COOCH_3)_2$, modifications thereto and derivatives thereof. The preparation of a starburst dendrimer-type backbone molecule through four successive generations is described in Examples 10–14 hereunder.

Macrocyclic Chelants

The macrocyclic chelant moieties in the polychelants of this invention preferably derive from macrocyclic chelants which have a reactive carboxyl or amine group which is not essential for metal coordination bonding. The reactive group can be one of the groups which in the free chelant can function as a metal coordinating group so long as the backbone conjugated chelant moiety retains the ability to complex metal ions. Alternatively the reactive group can be a substituent of a side chain of the chelant.

More particularly, as used herein, a macrocyclic chelant is defined as a chelant having one continuous, linked, closed backbone consisting of donor atoms, such as for example N, P, B, O, S and As, spaced by carbon atoms, e.g. carbons of optionally substituted methylene or cyclic, e.g. aromatic, groups or chains thereof, particularly preferably optionally substituted $C_{2-4}$ alkylene chains. Any of the methylene groups or donor atoms, where permitted by valence conditions, can be substituted so long as the closed chain of the macrocycle remains intact.

In one preferred embodiment of the invention, the macrocyclic chelants are of formula III

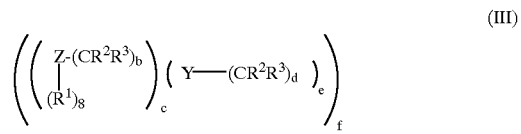

where a, b, d and e are independently zero or a positive integer, for b or d preferably 1, 2, 3 or 4; c and f are positive integers; the sum of all c's being at least 3, preferably 3, 4 or 5; the sum of b+d is at least 1; each Z is independently a nitrogen, oxygen, sulphur, phosphorus, boron or arsenic, preferably at least two, especially at least 3 of these being nitrogen; each Y is independently an optionally substituted 5 to 7 membered carbocyclic or heterocyclic ring;

where present is independently hydrogen, optionally hydroxylated, optionally alkoxylated alkyl optionally carrying a group CO—G where G is $OR^2$ or $NR^2{}_2$ and where Z is phosphorus optionally also oxo, at least 3 $Z(R^1)_0$ moieties preferably having Z as nitrogen, a=1 and $R^1$ as an optionally substituted G—CO—alkyl group; $R^2$ and $R^3$ which may be the same or different each independently is hydrogen, optionally alkoxylated, optionally hydroxylated alkyl, aryl, alkaryl or aralkyl or $R^3$ may also represent or be substituted by a group CO—C; and $NR^2{}_2$ may also represent a nitrogen-attached optionally substituted 5 to 7 membered heterocyclic ring optionally containing a further nitrogen oxygen, or sulphur ring heteroatom; and where in place of two $CR^2R^3$ groups, separated in either direction by at least one Z group, there may optionally be a bridging structure of formula

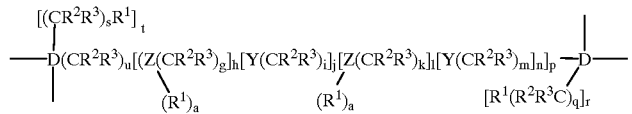

where u, g, h, i, j, k, l, m, n, q, r, s and t is each independently zero or a positive integer, for u, g, i, k and m preferably 1,2,3 or 4; p is a positive integer; h+l+j+n≧1, preferably p(h+l)≧1; and each D is independently boron, carbon, nitrogen, phosphorus or PO.

Preferred identities for the ring moieties Y include

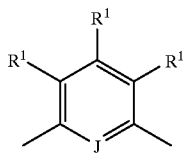

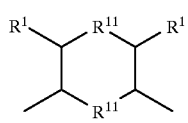

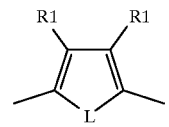

where J is CH, COH or N;
$R^{11}$ is $CH_2$, CHOH, $NR^1$, O or S; and
L is O or S.

Preferred identities for the heterocyclic moieties $NR^2{}_2$ include

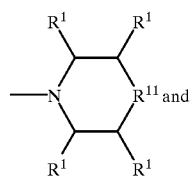

e.g.

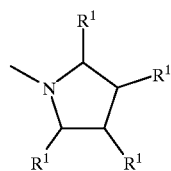

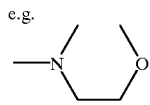

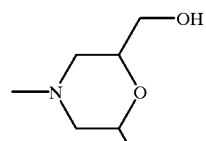

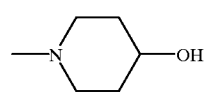

As indicated above, the macrocyclic chelant may include a second "cycle" which is created by linking the branches from two or more backbone atoms.

In the macrocyclic chelants, alkyl and alkylene moieties, unless specified otherwise, preferably contain up to 8 carbon atoms, especially preferably up to 4 carbons. Hydroxy or alkoxy substituted moieties may be mono- or poly-substituted and substitution by both is contemplated. Any aryl moieties are preferably $C_{6-10}$ carbocyclic or 5 or 6 membered heterocyclic rings. In the macrocycle, backbone heteroatoms, e.g. N,P,O and S are preferably separated by 1 to 8, especially preferably 2 to 6 carbon backbone atoms and, as mentioned, the macrocyclic chelant preferably contains at least 3 carboxyl groups or carboxyl derivative groups. Macrocyclic polychelants containing at least three ring nitrogen attached carboxyalkyl, especially carboxymethyl, groups are particularly preferred.

Linkage of the macrocyclic chelant to the backbone molecule may be effected through any reactive group, e.g. an $R^1$ or $R^3$ group, particularly preferably a CO—G group containing $R^1$ group.

Particularly preferably macrocyclic chelants include those of formula IV

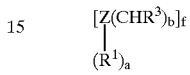

where each Z is N,O or S, preferably all or all but one Z being N;
each b is independently 2,3 or 4, preferably 2 or 3;
f is 3 or 4, preferably 4;
each $R^1$ is independently hydrogen, $C_{1-3}$ alkyl or an optionally branched, optionally hydroxylated CO—C—alkyl group; and each $R^3$ is independently hydrogen or a hydroxyalkyl group.

Thus in particular, the macrocyclic chelants include the polyazacycloalkanepolycarboxylates, hexaazamacrocycles (HAMs) and cryptates including sepulchrates and carcophagines.

Exemplary polyazacycloalkanepolycarboxylates include 1,4,7,10-tetraazacyclododecanetetraacetic acid (DOTA), 1,4,7,10-tetraazacyclododecane-1,4,7-triacetic acid (DO3A), 1-oxa-4,7,10-triazacyclododecanetriacetic acid (DOXA), 1,4,7-triazacyclononanetriacetic acid (NOTA) and 1,4,8,11-tetraazacyclotetradecanetetraacetic acid (TETA). Additionally, the novel tetraazacycloalkanepolycarboxylates, DOTA-N-(2-aminoethyl)amide and DOTA-N(2-aminophenethyl)amide are also contemplated.

The preparation of the tetraazacycloalkanepolycarboxylate ligands is well known. Synthesis of DOTA is described in U.S. Pat. No. 4,647,447 (Gries et al.) U.S. Pat. No. 4,639,365 (Sherry) and by Decreux et al. in Inorg. Chem. 19:1319 (1980). Additionally, DOTA is available commercially from Parrish Chemical Co., Orem, Utah. Preparation of DO3A is described in EP-A-292689 (Squibb). Desreux, Inorg. Chem., 19:1319 (1980); Bryden et al, Anal. Chem, 53:1418 (1981); Delgardo et al, Talanta, 29:816 (1982); Cacheris et al, Inorg. Chem, 26:958 (1987); Moi et al, Inorg. Chem, 26:3458 (1987) and Meares et al, Acc. Chem. Res., 26:3458 (1987) describe the properties and chemistry of the macrocyclic ligands DOTA, NOTA, TETA and their backbone-derivatized analogs, including the preparation of NOTA and TETA. U.S. Pat. No. 4,678,667 (Meares et al.) teaches the preparation of a number of macrocyclic, side chain-derivatized ligands including DOTA and TETA. Derivatization of DOTA to form DOTA-N-(2-aminoethyl)amide and DOTA-N(4-aminophenethyl)amide is described in detail hereinafter in Examples 2 and 3, respectively. The above cited references and all other references mentioned herein are hereby incorporated by reference in their entirety.

The hexaazamacrocycles include the series of $N_6$ macrocyclic chelates described in DeCola et al. in Inorg. Chem., 25:1729 (1986). That article also describes preparation of the HAMs and is incorporated herein by reference in its entirety.

Cryptates are polycyclic ligands which include sepulchrates, sacrophagines and macrocyclic polyethers (crown ethers) and macrobicyclic ligands. Preferred macrocyclic polyether cryptates include side-chain derivatized primary amine and carboxylate cryptates.

The sepulchrates include derivatives of the octaazamacrobicyclic system such as 1,3,6,8,10,13,16,19-octaazabicyclo[6,6,6]eicosane. Primary amine and carboxylate derivatives of these chelates are especially preferred. Synthesis of the chelates, as the cobalt complexes, is described in J. Amer. Chem. Soc., 104:6016 (1982). The sarcophagines include derivatives of the hexaazamacrobicyclic system such as 3,6,10,13,16,19-hexaazabicyclo[6,6,6]eicosane. Synthesis of sepulchrates and sarcophagines are described by Creaser et al. in J. Amer. Chem. Soc., 104:6016 (1982) and Geue et al. in J. Amer. Chem. Soc., 106:5478 (1984), respectively. Izatt and Christensen, Eds., Synthetic Multidentate Compounds, Academic Press (1978) and Lehn et al, Acc. Chem. Res., 11:49 (1978) describe synthesis of cryptates. Cotton & Wilkinson "Advanced Inorganic Chemistry" describe a general method of crown ether template synthesis for preparing encapsulating nitrogen-containing macrocycles. Those references are incorporated herein by reference in their entirety.

The products formed by reacting macrocycles containing at least one carboxylate group capable of activation by haloformate are themselves useful intermediates for preparing novel compounds. For example macrocycle dimers can be prepared by reacting said intermediate with a second macrocycle containing a primary amine group, resulting in a dimer linked through an amide moiety.

Metal Ions

Metals that can be incorporated, through chelation, include lanthanides and other metal ions, including isotopes and radioisotopes thereof, such as, for example, Mg, Ca, Sc, Ti, B, V, Cr, Mn, Fe, Co, Ni, Cu, Zn, Ga, Sr, Y, Zr, Tc, Ru, In, Ht, W, Re, Os, Pb and Bi. Particularly preferred radiisotopes of some of the foregoing include $^{153}$Sm, $^{66}$Cu, $^{67}$Cu, $^{67}$Ga, $^{68}$Ga, $^{89}$Sr, $^{88}$Y, $^{90}$Y, $^{99m}$Tc, $^{97}$Ru, $^{103}$Ru, $^{111}$In, $^{186}$Re, $^{188}$Re, $^{203}$Pb, $^{211}$Bi, $^{212}$Bi, $^{213}$Bi, and $^{214}$Bi. The choice of metal ion for chelation by polychelants of the invention will be determined by the desired therapeutic or diagnostic application.

Site-Directed Macromolecules

The site-directed macromolecules used in the compositions of this invention can be any macromolecules that are naturally concentrated in a selected target organ, tissue, cell or group of cells, or other location in a mammalian body, in vivo. These can include proteins, peptides, lipoproteins, glycoproteins and hormones. Exemplary site-directed proteins include polymerized fibrin fragments (e.g., $E_1$), serum amyloid precursor (SAP) proteins, low density lipoprotein (LDL) precursors, serum albumin, surface proteins of intact red blood cells, receptor binding molecules such as estrogens, liver-specific proteins/polymers such as galactosyl-neoglycoalbumin (NGA) (see Vera et al. in Radiology 151: 191 (1984)) N-(2-hydroxy-propyl) methacrylamide (HMPA) copolymers with varying numbers of bound galactosamines (see Duncan et al., Biochim. Biophys. Acta, 880:62 (1986)), and allyl and 6-aminohexyl glycosides (see Wong et al., Carbo. Res., 170:27 (1987)), and fibrinogen.

The site-directed protein can also be an antibody. The choice of antibody, particularly the antigen specificity of the antibody, will depend on the desired use of the conjugate. Monoclonal antibodies are preferred over polyclonal antibodies.

Human serum albumin (HSA) is a preferred protein for the study of the vascular system. HSA is available commercially from a number of sources including Sigma Chemical Co. Preparation of antibodies that react with a desired antigen is well known. Antibody preparations are available commercially form a variety of sources. Fibrin fragment $E_1$ can be prepared as described by Olexa et al. in J. Biol. Chem., 254:4925 (1979). Preparation of LDL precursors and SAP proteins is described by de Beer et al. in J. Immunol. Methods, 50:17 (1982). The above described articles are incorporated herein by reference in their entirety.

Method of Preparing Complex: General Order

In general, magnifiers are synthesized by conjugating the chelants to the backbone molecule prior to conjugating the backbone molecule to the site-directed macromolecule to produce a bifunctional polychelant. In most cases, the reaction conditions used for joining the chelants to the backbone molecule would denature proteins. Therefore, to preserve its tertiary structure and biological function an antibody or other site-directed protein will not generally be conjugated to a backbone molecule before the chelant groups have been loaded onto that backbone molecule, unless of source this can be done without denaturing the protein. The metal ions can be added to form the metal complex of the polychelants prior to or following conjugation of the magnifier to the site-directed macromolecule. Preferably, the metal will be added prior to conjugation of the magnifier polychelant to most proteins, particularly antibodies, in particular to avoid adventitious binding of the metal to the protein. However, for some metal ions such as radionuclides with a short half-life, metallation will preferably be performed following conjugation, just prior to use.

Linking the Macrocyclic Chelants to the Backbone Molecule

While in general well known methods can be used to join the macrocyclic chelants to backbone molecules, one particularly important aspect of the present invention is that it provides a simple and straightforward means of attaching macrocyclic chelants to backbone polyamine molecules. Thus while for preferred macrocyclic chelants such as DOTA the conventional mixed anhydride and cyclic anhydride conjugation techniques are ineffective, we have found that modifying the mixed anhydride procedure by reacting a polycarboxylic macrocyclic chelant in an anhydrous medium with an amine base of sufficient strength to abstract all the carboxyl protons (i.e. a high enough pka) yields an amine salt which can react with an alkylhaloformate to produce an activated anhydride capable of conjugating to the backbone polyamine without causing the undesired cross-linking associated with prior art bifunctional polychelants. For most macrocyclic chelants tetramethylguanidine or an amine base of similar strength will be the preferred base.

More complex conjugation techniques, involving for example the use of macrocyclic chelants backbone derivatized in a manner analogous to that of Meares et al. (supra) may of course be used but the increased cost and complexity of the overall production makes this a less desirable route. Similarly the chelants can be attached to the backbone polymer by a haloacetylhalide, a phosgene or a thiophosgene method depending on the available reactive group on the chelating agent.

For macrocycles with a pendant carboxylate, including but not limited to DOTA, TETA, TRITA (1,4,7,10-tetraazacyclotridecanetetraacetic acid) and NOTA, one of the coordinating carboxylates can form an entity which can react with a primary amine group of the backbone polymer. Methods of forming a reactive entity from a carboxylate group include the modified mixed anhydride reaction for example using isobutylchloroformate (IBCF), or the formation of an "activated ester" using a carbodiimide (DCC or EDAC, cf. Pierce Catalog (1988), p. 252 and 253). Both reaction sequences give rise to a backbone polymer multiply substituted with the macrocyclic chelant moieties through stable amide linkages. The modified mixed anhydride method however is the preferred method for use in joining the carboxylate-containing macrocyclic chelants to the backbone polymer.

The modified mixed anhydride reaction is performed in an anhydrous solvent preferably with a melting point below 5° C., cooled to a temperature not lower than 5° C. or greater than about 55° C. above its freezing point. The solubilization of the chelant in the appropriate solvent is conveniently effected by preparation of the amine salt of the chelant using the amine base in situ.

The choice of base is determined by the pKa of the relevant carboxylates. For most macrocycles, tetramethylguanidine (TMG) is especially preferred. In general, bases will conveniently be selected from those bases whose pKa value exceeds the highest pKa of the macrocyclic chelant by at least 0.5, preferably 0.8, especially preferably at least 1.0. Amine bases having pKa's of at least 11, especially at least 11.3, particularly at least 12, are particularly preferred and besides TMG particular mention may be made of piperidine, quinuclidine and N-ethylpiperidine and more especially DBU (1,8-diazabicyclo[5.4.0]undec-7-ene) and DBN (1,5-diazabicyclo[4.3.0]non-5-ene). Further bases are listed by Martell and Smith in "Critical Stability Constants" Vol. 5, first supplement, Plenum Press, NY 1982.

The appropriate quantity of neat (chilled) alkylhaloformate is now added with stirring and the original temperature of the solvent is maintained by cooling, e.g. by addition of coolant, if required. Isobutylchloroformate is especially preferred. The resulting activated anhydride of the macrocyclic chelant can be reacted with one or more amine-containing macrocycles to form dimers, trimers and/or oligomers, or it can be reacted with the free base form of an amine-containing polymer to form a magnifier polychelant. The magnifier polychelant, for most applications, is metallated at this point and purified by chromatography or crystallization to remove excess metal ions and lower molecular weight metal complexes. For use with target-specific macromolecules the magnifier polychelant or the at least partially metallated form thereof, still containing at least one free amine, is conjugated to the macromolecule, for example by reaction with one of many well-known heterobifunctional coupling agents to effect a link to the macromolecule. In situations where prior metalliation is not appropriate, e.g. with radionuclide metal ions with short-lives, the bifunctional polychelant can be prepared using a metal-free magnifier and coupling as described above, followed by metallation (vide infra) and final rapid, simple purification by chromatography or filtration.

The macrocyclic chelants can also be linked to the backbone polymer through a non-coordinating primary amine group. Macrocyclic chelants having a non-coordinating primary amine group include primary amine side-chain-derivatized DOTA macrocycles, primary amine-derivatized DO3A, and primary amine-derivatized hexaaza and octaaza macrocycles and macrobicycles (the HAMs, sepulchrates and sarcophagines) as well as the broad class of derivatized crown ether cryptates.

The non-coordinating primary amine group on these chelants can be reacted with a haloacetylhalide under well-known conditions to form a haloacetamide. The haloacetamide can react with a primary amine of the backbone polymer to form a stable amide linkage between the chelant and the polymer. The haloacetylhalide method described in De Riemer et al, J. Labelled Compd. Radiopharm., 18:1517 (1981) can be used to join amine-containing chelants to the backbone polymer.

Amine groups on a macrocyclic chelant can also be reacted with phosgene to generate a reactive isocyanate group, or with thiophosgene to generate a reactive isothiocyanate group. Those groups can react with a primary amine of the backbone polymer to form a stable urea or more stable thiourea linkage, respectively, between the ligand and the backbone polymer. Gansow, Inorg. Chimica Acta, 91:213 (1984) and Moi et al, J. Amer. Chem. Soc., 110:6266 (1988) describe methods of linking chelants to proteins having an amine group through formation of the isocyanate or isothiocyanate moieties using the phosgene or thiophosgene methods, respectively. See also Desreux, Inorg. Chem., 19:1319 (1980); Bryden et al, Anal. Chem, 53:1418 (1981); Delgardo et al, Talanta, 29:815 (1982); Cacheris et al, Inorg. Chem., 26:958 (1987); Moi et al, Inorg. Chem, 26:3458 (1987) and Meares et al, Acc. Chem. Res., 26:3458 (1987).

Metallation

As indicated earlier the choice of metal ions to be chelated by the polychelants of the invention depends upon the diagnostic or therapeutic technique for which the resulting polychelate is to be used. For MRI, the metal ions should be paramagnetic, and preferably non-radioactive. For X-ray and ultrasound imaging, heavy metal ions, e.g. with atomic numbers of at least 37, preferably at least 50, should be used, again preferably non radioactive species. For scintigraphy or radiotherapy the metal ions should of course be ions of radioactive isotopes.

Methods of complexing metal ions with chelants and polychelants are within the level of skill in the art. Each of the metals used can be incorporated into a macrocyclic chelant moiety by one of three general methods: direction incorporation, template synthesis and/or transmetallation. Direct incorporation is preferred.

The metal ions Fe(III), Cr(III), Mn(II), Mg(II), Pb(II), Bi(III) and the lanthanides can be directly incorporated into polyaminopolycarboxylates by the following general procedure. A water-soluble form of the metal, generally an inorganic salt, is dissolved in an appropriate volume of distilled, deionized water. The pH of the solution will be below 7. An aqueous solution containing an equimolar amount of the polychelant is added to the metal solution at room temperature while stirring. The pH of the mixture is raised slowly by addition of base, typically 0.1 M NaOH, until the donor groups of the polychelant are deprotonated, generally in the pH range of 7 to 9, depending on the chelant moieties. Particular care must be taken with the lanthanide ions to maintain the pH below 8 to avoid precipitation of the metal hydroxide. Metal incorporation into DOTA derived and related macrocyclic chelant moieties will normally be a slow process, as described in the references cited below. Specific examples of the procedure are contained in the Examples hereto and in the following references.

Choppin et al, J. Inorg. Nucl. Chem., 33:127 (1971), Margerum, Rec. Chem. Prog., 24:237 (1973) and D'Olieslager et al, J. Inorg. Nucl. Chem., 35:4255 (1973) describe direct incorporation of the lanthanides into polyaminopolycarboxylates. Margerstadt, Mag. Res. Med., 3:808 (1986) and WO-A-87/06229 describe incorporation of Gd(III) into DOTA. A method of preparing Bi and Pb complexes of DOTA is described by Kumar et al, J. Chem. Soc. Chem. Commun., 3:145 (1989). The above references are incorporated herein by reference in their entirety.

Direct incorporation of Hf, Zr, W, Hg and Ta can be performed according to well known methods. See, for example, U.S. Pat. No. 4,176,173 (Winchell).

Transmetallation is useful when the metal ions needs to be reduced to a more appropriate oxidation state for the donor atoms of the chelant moiety to bind. For example, to incorporate $^{99m}$Tc or $^{186/188}$Re, the metal ion must be reduced to Tc(V) or Re(V) by the use of reducing agents such as $SnCl_2$ or systeine by well known methods. This method requires formation of an intermediate complex. A typical example is the reduction of $^{99m}$Tc with Sn in the presence of a weakly coordinating ligand such as glucoheptonate prior to complexation with chelants such as DOTA. These methods are well known in the radiopharmaceutical art. $^{67}$Cu utilizes tetraamine chelates such as tet A or tet B (see Bhardaredj et al., JACS, 108:1351 (1986)) to stabilize Cu(II) for reaction with stronger-binding chelants.

Template synthesis can be performed by the method described by Smith et al. in Inorg. Chem., 24:3469 (1985) and 27:4154 (1988). In the case of the HAM systems, the metal ion is incorporated into the macrocyclic chelant by building the chelant around the metal ion via template synthesis. Well-known template synthesis methods are described by Smith et al. (Supra) for lanthanide template syntheses. The sepulchrate and sarcophagine macrobicyclic chelants may be similarly prepared by a template synthesis around Co. The Co is removed by reduction to Co(II) and extraction with 15 M HBr. The metal-free chelant may then be metallated via reaction with a simple metal salt by refluxing in methanol, or by transmetallation from a donor complex such as glucoheptonate, ascorbate, acetate or citrate salts. Use of triflate and/or perchorate salts are preferred.

The broad class of crown ethers and cryptates, especially those containing N, O, and S, can be metallated in a similar fashion using one or more of the methods described above.

Attaching Backbone to Protein

Methods for attaching backbone polymers to antibodies and other proteins are within the level of skill in the art. Such methods are described in Pierce 1989 Handbook and General Catalog and the references cited therein, Blatter et al, Biochem., 24:1517 (1985) and Jue et al, Biochem., 17:5399 (1978). The references cited above are incorporated herein by reference in their entirety.

Formulation

The metal chelates of the polychelants of the invention, especially the bifunctional polychelants but optionally also the magnifier polychelants, may be administered to patients for imaging in amounts sufficient to yield the desired contrast with the particular imaging technique. Generally dosages of from 0.001 to 5.0 mmoles of chelated imaging metal ion per kilogram of patient bodyweight are effective to achieve adequate contrast enhancements. For most MRI applications preferred dosages of imaging metal ion will be in the range from 0.02 to 1.2 mmoles/kg bodyweight while for X-ray applications dosages of from 0.5 to 1.5 mmoles/kg are generally effective to achieve x-ray attenuation. Preferred dosages for most X-ray applications are from 0.8 to 1.2 mmoles of the lanthanide or heavy metal/kg bodyweight.

Where a contrast agent is required to collect in the blood pool or in the extracellular fluid, then preferably a low generation dendrimeric backbone will be used, for example a zero or first generation dendrimeric backbone. Such polychelants have enhanced relaxivity compared to known blood pooling and ECF contract agents and thus a lower effective dosage can be administered.

For X-ray applications, to extend the photon energy range over which the polychelates of the invention are optimally effective the polychelates used may be of two or more different metals, either as mixtures of homopolychelates or as a heteropolychelate.

The compounds of the present invention may be formulated with conventional pharmaceutical or veterinary aids, for example stabilizers, antioxidants, osmolality adjusting agents, buffers, pH adjusting agents, etc., and may be in a form suitable for parenteral or enteral administration, for example injection or infusion or administration directly into a body cavity having an external escape duct, for example the gastrointestinal tract, the bladder or the uterus. Thus the compounds of the present invention may be in conventional pharmaceutical administration forms such as tablets, capsules, powders, solutions, suspensions, dispersions, syrups, suppositories etc.; however, solutions, suspensions and dispersions in physiologically acceptable carrier media, for example water for injections, will generally be preferred.

The compounds according to the invention may therefor be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized. Suitable additives include, for example, physiologically biocompatible buffers (as for example, tromethamine hydrochloride), additions (e.g., 0.01 to 10 mole percent) of chelants (such as, for example, DTPA, DTPA bisamide or non-complexed magnifier polychelant) or calcium chelate complexes (as for example calcium DTPA, CaNaDTPA-bisamide, calcium-magnifier polychelant or CaNa salts of magnifier polychelants), or, optionally, additions (e.g., 1 to 50 mole percent) of calcium or sodium salts (for example, calcium chloride, calcium ascorbate, calcium gluconate or calcium lactate combined with metal chelate complexes of magnifier ligands, and the like).

If the compounds are to be formulated in suspension form, e.g., in water or physiological saline for oral administration, a small amount of soluble chelate may be mixed with one or more of the inactive ingredients traditionally present in oral solutions and/or surfactants and/or aromatics for flavoring.

For MRI and for X-ray imaging of some portions of the body the most preferred mode for administering metal chelates as contrast agents is parenteral, e.g., intravenous administration. Parenterally administratable forms, e.g., intravenous solutions, should be sterile and free from physiologically unacceptable agents, and should have low osmolality to minimize irritation or other adverse effects upon administration, and thus the contrast medium should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The solutions can contain preservatives, antimicrobial agents, buffers and antioxidants conventionally used for parenteral solutions, excipients and other additives which are compatible with the chelates and which will not interfere with the manufacture, storage or use of products.

Viewed from a further aspect the invention provides an image enhancing or therapeutic composition comprising a metal chelate of a polychelant of the invention or a salt thereof together with at least one pharmaceutical carrier or excipient.

Viewed from a still further aspect the invention provides the use of a polychelant according to the invention or a chelate or salt thereof for the manufacture of an image enhancing contrast medium or a therapeutic composition.

Viewed from another aspect the invention provides a method of generating an image of a human or non-human animal, especially mammalian, body which method comprises administering to said body an image enhancing amount of a polychelate according to the invention or a salt thereof and thereafter generating an image e.g. an MR, X-ray, ultrasound or scientigraphic image, of at least a part of said body.

Viewed from a still further aspect the invention provides a method of radiotherapy of the human or animal body said method comprising administering to said body a therapeutically effective amount of a radioactive metal chelate of a polychelant according to the invention.

Viewed from a yet still further aspect the invention provides a method of producing a polychelant according to the invention or a chelate thereof, said method comprising conjugating to a backbone polyamine a plurality of macrocyclic chelants, optionally conjugating the resulting polychelant to a site-specific macromolecule, and optionally metallating said polychelant before or after conjugation to a said macromolecule.

Viewed from another aspect the invention provides a detoxification composition comprising a polychelant according to the invention or a weak chelate complex or salt thereof with physiologically tolerable counterions, together with a pharmaceutical carrier or excipient.

Viewed from a still further aspect, the invention provides a method of metal detoxification comprising administering to a human or non-human animal a detoxifying amount of a polychelant according to the invention or a weak chelate complex or salt thereof with physiologically tolerable counterions.

This invention is further illustrated by the following specific but non-limiting examples. Temperatures are given in degrees Celcius and concentrations as weight percentages unless otherwise specified.

EXAMPLE 1

Preparation of DOTA Carboxycarbonic Anhydride

DOTA (0.808 g, 2.0 mmol) was suspended in 5.0 ml of anhydrous acetonitrile. Tetramethylguanidine (1.00 ml, 8.0 mmol) was added and the mixture stirred under an atmosphere of nitrogen for about 5 minutes at ambient temperature until the DOTA was dissolved. The resulting solution was cooled to −25° C. under an atmosphere of nitrogen and stirred while adding 0.260 ml (2.0 mmol) of isobutylchloroformate (IBCF), slowly over 5 minutes. The resulting slurry was stirred 1 hour at −25° C.

EXAMPLE 2

Preparation of DOTA-N(2-aminoethyl)amide

To the cold slurry from Example 1 was added a solution of mono-BOC-ethylenediamine (0.320 g, 2 mmol) in 2 ml acetonitrile and the mixture stirred 6 to 12 hours at ambient temperature. The mixture was brought to 20 ml with $H_2O$, treated with 6 ml of concentrated HCl, and then stirred overnight to effect removal of the protecting group. The solution was evaporated to dryness. The residue was purified by ion exchange chromatography on DOWEX AGI-X8 resin. Evaporation of the appropriate fractions afforded 0.35 g of a semi-crystalline glass. $^1H$ NMR demonstrated the expected product, as well as some residual acetate (from chromatography).

EXAMPLE 3

Preparation of DOTA-N-(4-aminophenethyl)amide

To the cold slurry from Example 1 is added a solution of 4-nitrophenethylamine (0.332 g, 2 mmol) in 4.0 ml acetonitrile. The mixture is stirred 6 to 12 hours at ambient temperature. After evaporation to dryness, the residue is redissolved in water and pH adjusted to 10.5 with NaOH to form a mixture which is extracted with ethyl acetate to remove unreacted amine. The product, DOTA-N-(4'-nitrophenethyl)amide, is isolated by ion exchange chromatography on DOWEX AGI-X8 resin. Following evaporation of the appropriate fractions, the residue is dissolved in water in a Parr reaction, and 0.1 g of 5% palladium on activated carbon is added to form a reaction mixture. The reaction mixture is hydrogenated at 30–40 psi until the pressure ceases to drop. The product is isolated by filtering off catalyst and evaporating the filtrate to dryness.

EXAMPLE 4

Activation of Amino Group of DOTA-N-(2-aminoethyl)amide with Thiophosgene—Conversion to Isothiocyanate Groups An aqueous solution of the product prepared in Example 2 is added to an equal volume of chloroform containing thiophosgene and sodium biacarbonate, each of which is in four-fold molar excess with respect to the target amino group. The mixture is stirred vigorously for 1–2 hours, and the phases are separated. The aqueous phase is washed with chloroform, and then it is evaporated to dryness. The resultant solid product is washed with ethanol and dried in vacuo.

The procedure is repeated, substituting the product of Example 3 for the product of Example 2.

EXAMPLE 5

Activation of Amino Group of DOTA-N(2-Aminoethyl)Amide with Bromoacetyl Chloride—Conversion to Bromoacetamide Groups An aqueous solution of the product prepared in Example 2 (20 mg/ml) which also contains triethylamine (20 mg/ml) is treated with an equal volume of a chloroform solution of bromoacetyl chloride (30 mg/ml), and the two-phase mixture is stirred vigorously for 1–2 hours. Water is added, to double the volume of the aqueous phase, and the mixture is extracted with ethyl acetate. The aqueous phase is evaporated to dryness and the residue triturated with acetone and dried in vacuo.

The procedure is repeated, substituting the product of Example 3 for the product of Example 2.

EXAMPLE 6

Preparation of DOXA and DOXA carboxycarbonic ahydride (a) Synthesis of 1-oxa-4,7,10-trizacyclododecane-4, 7,10-triacetic acid (DOXA)

This compound was prepared as described by Amorim M.T.S. et al. in Talanta 35(9): 741–745 (1988).

(b) DOXA carboxycarbonic anhydride

DOXA (4 mmol, 1.38 g) is suspended in 7.0 ml of acetonitrile. Tetramethylguanidine (TMG, 12 mmol, 1.38 g, 1.5 mL) is added and the mixture refluxed until homogeneous. The resulting solution is cooled to −30° C. under an atmosphere of nitrogen and stirred while adding isobutyl-chloroformate (4 mmol, 0.520 mL) slowly over 5 min. The resulting slurry is stirred for 1 hour at −30° C.

EXAMPLE 7

Preparation of TETA and TETA carboxycarbonic anhydride (a) Synthesis of 1,4,8,11-tetraazacyclotetradecane-N,N',N'',N'''-tetraacetic acid (TETA)

This material was prepared according to the method of Delgado et al., Talanta 29: 815–822 (1982).

(b) TETA carboxycarbonic anhydride

TETA (4.4 mmol, 1.9 g) was suspended in 10 mL of acetonitrile, Tetramethylguanidine (TMG, 17.6 mmol, 2.2 mL) was added and the slurry refluxed for 1 hour. The resulting solution was cooled to ambient temperature and dried over 4 Å molecular sieves for 4–8 hours. The solution was decanted form the sieves and cooled to −30° C. under an atmosphere of nitrogen, then stirred while adding 4.4 mmol, 0.510 mL of isobutyl-chloroformate slowly over 5 min. The resulting mixture was stirred 1 hour at −30° C. and allowed to warm to −10° C.

EXAMPLE 8 a) Preparation of Core Adduct for PAMAM backbone polymer 6.6 g gaseous $NH_3$ was dissolved in 100 g methanol at 4° C. in approximately 30 minutes with stirring. The gas flow was monitored using bubbles in hood. The resultant solution was added dropwise to 195 g methyl acrylate over 3 hours 10 minutes. The maximum temperature observed was 30° C. and the mixture was stirred for 3 days. Residual methyl acrylate and methanol were removed using rotary evaporation (vacuum pump at approximately 5 mmHg, 38° C. for 1 hour) to yield 170 g of a clear, oily viscous solution $^1$H NMR demonstrated that there was not residual methyl acrylate in the end-product.

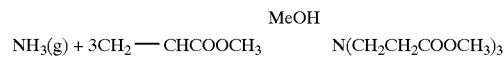

EXAMPLE 9 b) Preparation of first generation ($G_{1.0}$) PAMAM Derivative 29 g of the triester formed in Example 8 was combined slowly with 500 g ethylenediamine in 215 g MeOH. The mixture was allowed to stand for over 60 hours. Excess methanol and ethylenediamine were removed using rotary evaporation (60° C., 1–2 mmHg).

32.6 g of pale yellow thick syrup was obtained.

$^1$H NMR was used to confirm the identify of the reaction product.

EXAMPLE 10

Preparation of second generation $G_{2.0}$ PAMAM Derivative a) $G_{1.5}$ PAMAM Derivative 174 g methylacrylate was heated to 32° C. 32.6 g of the product from Example 9 was dissolved in 100 g methanol and this was added using a dropping funnel over 1½ hours to the methylacrylate with stirring under reflux. The mixture was stirred for a further 6 hours at 32° C., and then cooled to ambient temperatures and allowed to stand for 20 hours. Residual methanol/methylacrylate were removed by using a rotary vacuum pump at 50° C. $^1$H NMR confirmed the absence of methylacrylate. Theoretical yield 79.7 g. Obtained 78 g (98% of theory).

b) $G_{2.0}$ PAMAM Derivative 700 ml ethylenediamine were combined with 420 g methanol at ambient temperature. The mixture was heated by exothermic reaction, but was cooled to 40° C. after 1 hour. 78 g of the $G_{1.5}$ derivative from (a) was mixed into 100 g methanol to produce a bright yellow solution and was added to the ethylenediame/methanol mixture over 10 minutes with stirring. The temperature increased during addition to 50° C. The mixture was allowed to stand for 3 days after which rotary evaporation was used to remove any excess ethylenediamine and methanol (5 mmHg).

Theoretical yield 91.8 g. Obtained 92 g.

EXAMPLE 11

Preparation of third generation ($G_{3.0}$) PAMAM Derivative a) $G_{2.5}$ PAMAM Derivative 200 g methylacrylate in a 2 liter round bottomed flask was placed in a flask equipped with a stirrer and condenser. 92 g of the product obtained from Example 10 dissolved in 300 ml MeOH was added over 2 hours. During addition, the temperature rose from 20° C. to 35° C. The mixture was stirred at ambient temperature for 2 hours. Residual methylacrylate and methanol were removed by rotary evaporation. $^1$H NMR was used to confirm the purity of the product.

|       | C     | H    | N     |
|-------|-------|------|-------|
| Calc: | 53.78 | 8.02 | 12.03 |
| Found:| 52.67 | 8.01 | 10.32 | b) $G_{3.0}$ PANAM Derivative 1400 ml ethylenediamine was combined with 700 mls methanol in a 3 liter flask equipped with a stirrer, thermometer and condenser. The mixture heated exothermically to 70° C., and dropped to 40° C. after ¼ hour. 124 g of the product from (a) was dissolved in 250 mls methanol, stirred until completely solubilised and added dropwise at ambient temperature over 40 hours, to the ethylenediamine/methanol mixture. After being stirred for 24 hours, excess methanol and ehtylenediamine was removed by rotary evaporation, 70° C. 180 g of a yellow oil/gum was obtained.

EXAMPLE 12

Preparation of fourth generation ($G_{4.0}$) PAMAM Derivative a) $G_{3.5}$ PAMAM Derivative 92 g of the end-product from Example 11 was dissolved in methanol and was added slowly over 2 hours to a stirred solution and methylacrylate present in 40-fold excess (140 g) at ambient temperature. The reaction mixture was left for 48 hours, with stirring. Rotary evaporation was used to remove any excess methylacrylate and methanol. 160 g of a golden yellow residue (94% of theory) was obtained.

b) $G_{4.0}$ PAMAM Derivative 1600 ml ethylenediamine was added to 700 mls methanol with stirring. 100 g of the product from (a) in 500 ml methanol was added slowly thereto over 72 hours and was then stirred at ambient temperature for approximately 100 hours. Ethylenediamine was removed using a rotary evaporator. n-Butanol was added to azeotrope off any remaining ethylene. Excess n-butanol was removed by rotary evaporation.

EXAMPLE 13

Preparation of $G_{2.0}$ PAMAM—poly DOTA

The $G_{1.0}$ PAMAM dendrimer prepared in Example 10 (10 g, 0.01 mol) is combined with 12 equivalents of DOTA carboxycarbonic anhydride (0.13 mol) prepared as in Example 1, by slowly mixing a precooled (0° C.) acetonitrile solution (20 ml) of dendrimer to the DOTA mixed anhydride slurry over 10 minutes and gradually allowing the reaction mixture to warm to ambient temperature. The reaction mixture is worked up and purified according to the procedure developed for polylysine described in Sieving et al., Bioconj. Chem., 1,(1); 65–71 (1990).

EXAMPLE 14

Activation of Human Serum Albumin (HSA)

HSA contains one native thiolate group. This group was blocked by alkylation as described below. 50 ml of 0.05 M Tris-HCl, pH 7.3 was adjusted to pH 8.0 using 1.0 M Tris base. HSA (1 g, 15 μmol) was added to the solution. After stirring until homogeneous, the flask containing the solution was purged with dry nitrogen, sealed with a septum and wrapped in aluminum foil to exclude light.

A solution of iodoacetamide (15 mg, 80 μmol) in 4.0 ml of 1 N NaOH was added dropwise by using a syringe inserted through the septum. The resulting reaction mixture was stirred for 45 minutes at ambient temperature in the dark. The reaction mixture was dialyzed against 3.5 liters of 0.05 M sodium bicarbonate, pH 8.0, for 12 hours, with a buffer change at 6 hours. The dialystate was lyophilized to dryness to form a white fibrous mass.

The absence of free thiols in the preparation was demonstrated by the method of Ellman (see Arch. Biochem. Biophys. 74: 443 (1958)). The purity of the preparation was determined by measuring the specific absorbance of a 1 mg/ml solution of the product at 280 nm (1 cm path). The analysis showed that a purity of 99% with yield of 0.903 g was obtained.

100 mg of the above thiol-blocked HSA was dissolved in 50 ml of 60 mM triethanolamine, 7 mM monopotassium phosphate, 100 mM NaCl, 1 mM EDTA, pH 8.0. The solution was degassed for 10 minutes by stirring under vacuum, then covered with an atmosphere of nitrogen in a septum-sealed flask. After cooling the flask in an icebath, a solution of 2-iminothiolane (8.5 mg) in 100 μl of 1 M triethanolamine, pH 8.0 was added to the flask by syringe. The mixture was stirred for about 90 minutes at 0–4° C. After overnight dialysis against 3.5 liters of 0.08 M sodium phosphate, 0.5 mg/ml; EDTA, pH 8.0 with frequent buffer changes, spectrophotometric analysis by the method of Ellman demonstrated the presence of 2.7 thiols per mole of HSA.

Activation of Gadolinium Polychelates for Coupling to HSA

A sample of the polychelate is dissolved in $Na_2HPO_4$, pH 8. A solution of succinimidyl-4-(N-malaimidomethyl) cyclohexane-1-carboxylate (SMCC) in DMSO is added dropwise to form a mixture. The mixture is stirred for 30 minutes at ambient temperature to form a solution. The resulting solution is dialyzed for 12 hours against $H_2O$ with a single change at 6 hours to remove excess SMCC.

Coupling of Gadolinium Polychelates to HSA

The solutions prepared as described above are combined and stirred for 4 hours to form a mixture. The mixture is lyophilized. The resultant solid is dissolved in $H_2O$ and dialyzed for 6 hours against $H_2O$. The dialysate is chromatographed on Sephacryl S-300. The fractions with significant absorbance at 280 nm are pooled and lyophylized. A sample of this solid is dissolved in water (1 mg/ml) and assayed for HSA (using a spectrophotometer and measuring absorbance at 280 nm) and Gd (using directly coupled plasma atomic absorption (DCP-AA)) to determine the number of metal ions bound per mole HSA.

EXAMPLE 15

Activation of Antibody L6

Antibody L6 (5 Mg, 33 nmol) in 2.5 mL 60 mM triethanolamine, 7 mM monopotassium phosphate, 100 nM NaCl, 1 mM EDTA, pH 8, was degassed for 10 min by stirring under vacuum and then put under an atmosphere of $N_2$. After cooling for 30 min in an icebath, 70 μL of 2-iminothiolane HCl (2 μmol) in the same triethanolamine buffer was added. The mixture was stirred for 90 min at 0–4° C. The resulting mixture was then transferred into 150 mM NaCl, 80 mM sodium phosphate, 0.5 mg/ml EDTA pH 8, and concentrated by ultrafiltration. The concentrated antibody was diluted to 2.5 mL with the same buffer. Spectrophotometric analysis by Ellman's method demonstrated the presence of 2.2 thiols per molecule of antibody.

Activation of Gadolinium Polychelates for coupling to Antibody L6

A sample of the polychelate is dissolved in 0.008M $Na_2HPO_4$, pH 8. A solution of SMCC in DMSO is then added dropwise. The mixture is stirred for 30 min while protected from light. Excess SMCC and buffer salts are then removed by ultrafiltration using an Amicon centricon 30 microconcentrator (5000 rpm for 45 min, then repeated twice with $H_2O$ added to the concentrated polychelate). The polychelate is then diluted with deionized $H_2O$. Reaction of an aliquot of this polychelate with a known amount of 2-mercaptoethanol and measurement of the residual sulfhydryls by Ellman's method allows the number of maleimide residues per molecule of polychelate to be estimated.

Coupling of Gadolinium Polychelates to Antibody L6

The solutions prepared as described above are combined and stirred overnight. The mixture is concentrated by ultrafiltration and then chromatographed on Sephacryl S300. The fractions absorbing significantly at 280 nm are pooled and concentrated to a known volume.

I claim:

1. A dendrimeric backbone moiety-containing polychelant of the formula I $$B(L)_n \qquad (I)$$

where B is said dendrimeric backbone moiety, n is an integer having a value from 3 to 200, and each L is, independently, a macrocyclic chelant moiety linked to said dendrimeric backbone moiety via an amide group and capable of complexing metal ions, and metal chelates and salts thereof.

2. A polychelant as described in claim 1 wherein said dendrimeric backbone moiety is a dendrimeric polyamine backbone moiety linked to said macrocyclic chelant moieties through amide linkages.

3. A compound according to claim 1 wherein B is the residue of a zero to sixth generation starburst dendrimer.

4. A compound according to claim 1 wherein is 6 to 48.

5. A compound according to claim 1 wherein at least one of said chelant moieties is unmetallated.

6. A compound according to claim 1 wherein at least one of said chelant moieties is metallated by metal ions selected from the group consisting of the paramagnetic ions of Fe, Mn, Co, the ions of Bi, Hg, Os, Pb, Zr, and lanthanides and the radioactive ions of In, Tc, Y, Re, Pb, Cu, Ga, Bi and Sm.

7. A compound according to claim 1 wherein said backbone moiety is a polyaminoamido polymer or a derivative thereof.

8. A compound according to claim 7 wherein said backbone moiety is a first, second, third or fourth generation polyaminoamido, starburst dendrimer polymer.

9. A compound according to claim 1 wherein said macrocyclic chelant moieties are residues of macrocyclic chelants of formula III

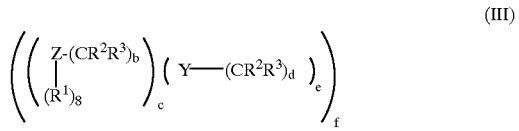

where a, b, d and e are independently zero or a positive integer; c and f are positive integers, the sum of all cs being at least 3; the sum of b+d is at least 1; each Z is independently a nitrogen, oxygen, sulphur, phosphorus, boron or arsenic; each Y is independently an optionally substituted 5 to 7 membered carbocyclic or heterocyclic ring;

$R^1$ where present is independently hydrogen, optionally hydroxylated, optionally alkoxylated alkyl optionally carrying a group CO—G where G is $OR^2$ or $NR^2_2$ and where Z is phosphorus optionally also oxo;

$R^2$ and $R^3$ which may be the same or different each independently is hydrogen, optionally alkoxylated, optionally hydroxylated alkyl, aryl, alkaryl or aralkyl or $R^3$ may also represent or be substituted by a group CO—G; and $NR^2_2$ may also represent a nitrogen-attached optionally substituted 5 to 7 membered heterocyclic ring optionally containing a further nitrogen, oxygen or sulphur ring heteroatom; and where in place of two $CF^2R^3$ groups, separated in either direction by at least one Z group, there may optionally be a bridging structure of formula

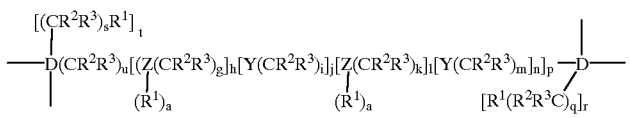

where u, g, h, i, j, k, l, m, n, q, r, s and t is each independently zero or a positive integer; p is a positive integer; $h+l+j+n \leq 1$; and each D is independently boron, carbon, nitrogen or phosphorus or PO.

10. A compound according to claim 1 wherein said macrocyclic chelants are selected from the residues of polyazacycloalkanepolycarboxylates, derivatized crown ethers, derivatized hexaazamacrocycles (HAMs), and derivatized cryptates, sepulchrates and sarcophagines.

11. A compound according to claim 9 wherein said macrocyclic chelants are selected from the residues of 1,4,7,10-tetraazacyclododecanetetraacetic acid (DOTA), 1,4,7,10-tetraazacyclododecane-1,4,7-triacetic acid (DO3A), 1-oxa-4,7,10-triazacyclododecane-triacetic acid (DOXA), 1,4,7-triazacyclononanetriacetic acid (NOTA), 1,4,8,11-tetraazacyclotetradecanetetraacetic acid (TETA), DOTA-N(2-aminoethyl)amide and DOTA-N-(2-aminophenethyl)amide.

12. A compound according to claim 1 wherein one or more of said macrocyclic chelant-carrying backbone moieties is conjugated to a macromolecule, or a chelate or salt thereof.

13. A compound according to claim 1 comprising a site-directed macromolecule capable of travelling to or binding specifically to targeted cells, tissues, organs or other locations in a mammalian body having conjugated thereto 1,2,3 or 4 said macrocyclic chelant moiety carrying backbone moieties, or a chelate or salt thereof.

14. A compound according to claim 12 wherein said macromolecule is selected from antibodies specific for a desired antigen, polymerized fibrin fragments, serum amyloid precursor proteins, low density lipoprotein precursors, serum albumin, surface proteins of intact red blood cells, hormones, liver-specific macromolecules, receptor binding proteins and fibrinogen.

15. A compound according to claim 14 wherein said macromolecule is a monoclonal antibody specific for a desired antigen.

16. A compound according claim 12 wherein said macromolecule is bound to said backbone moieties by heterobifunctional linking agents bonded via reactive linking groups selected from the group consisting of amide, maleamide, disulfide, thiourea, isothiocyanate, and ester groups.

17. An image enhancing or therapeutic composition comprising a metal chelate of a polychelant according to claim 1 or a salt thereof together with at least one pharmaceutical carrier or excipient.

18. A method of generating an image of a human or non-human animal body, which method comprises administering to said body a polychelate according to claim 1 or a salt thereof and thereafter generating an image of at least a part of said body.

19. A method of radiotherapy of the human or animal body, said method comprising administering to said body a radioactive metal chelate of a polychelant according to claim 1.

20. A detoxification composition comprising a polychelant according to claim 1 or a weak chelate complex or salt thereof with physiologically tolerable counterions, together with a pharmaceutical carrier or excipient.

21. A dendrimeric backbone moiety-containing polychelant comprising a dendrimeric backbone moiety and plurality of macrocyclic chelant moieties, each of said macrocyclic chelant moieties linked to the dendrimeric backbone moiety via an amide group and capable of complexing metal ions, and metal chelates and salts thereof.

22. A dendrimeric backbone moiety-containing polychelant of the formula I

where B is said dendrimeric backbone moiety, n is an integer that is not greater than 200, and each L is independently, a macrocyclic chelant moiety linked to said dendrimeric backbone moiety via an amide group and capable of complexing metal ions, and metal chelates and salts thereof.

23. A method of metal detoxification comprising administering to a human or non-human animal a detoxifying amount of a polychelant according to claim 1 or a weak chelate complex or salt thereof with physiologically tolerable counterions.

* * * * *